(12) United States Patent
Karmali (10) Patent No.: US 8,377,973 B2
(45) Date of Patent: Feb. 19, 2013

(54) COMPOSITIONS AND PROCESSES FOR PREPARING 5-AMINO OR SUBSTITUTED AMINO 1,2,3-TRIAZOLES AND TRIAZOLE OROTATE FORMULATIONS

(75) Inventor: Rashida A. Karmali, Brooklyn, NY (US)

(73) Assignee: Tactical Therapeutics Inc, New York, NY (US)

( * ) Notice: Subject to any disclaimer, the term of this patent is extended or adjusted under 35 U.S.C. 154(b) by 90 days.

(21) Appl. No.: 12/807,415

(22) Filed: Sep. 3, 2010

(65) Prior Publication Data

US 2011/0060142 A1    Mar. 10, 2011

Related U.S. Application Data

(63) Continuation-in-part of application No. 12/584,448, filed on Sep. 4, 2009, now abandoned.

(51) Int. Cl.
*A01N 43/64* (2006.01)
*A61K 31/41* (2006.01)

(52) U.S. Cl. ................................ 514/359; 548/255

(58) Field of Classification Search .......... 548/255
See application file for complete search history.

(56) References Cited

U.S. PATENT DOCUMENTS

| | | | | |
|---|---|---|---|---|
| 4,061,741 A | | 12/1977 | Wawretschek et al. | 424/232 |
| 4,590,201 A | * | 5/1986 | Bochis et al. | 514/359 |
| 5,132,315 A | * | 7/1992 | Kohn et al. | 514/359 |
| 5,359,078 A | | 10/1994 | Kohn et al. | 548/255 |
| 5,912,346 A | | 6/1999 | Wehrmann | 544/310 |
| 2006/0189640 A1 | * | 8/2006 | Karmali | 514/269 |

FOREIGN PATENT DOCUMENTS

WO    WO 9703668 A1 *  2/1997

OTHER PUBLICATIONS

H.G. Brittain, Preparation and Identification of Polymorphs and Solvatemorphs, in Preformulation in Solid Dosage Form Development 185-228, 194 (Moji Christianah Adeyeye and Harry G. Brittain eds., 2008).*
S.L. Morissette et al., Advanced Drug Delivery Reviews, 56, 275-300 (2004).*
S.R. Vippagunta et al., Advanced Drug Delivery Reviews, 48, 3-26 (2001).*
J.K. Guillory, Generation of Polymorphs, Hydrates, Solvates, and Amorphous Solids, in Polymorphism in Pharmaceutical Solids 183-220 (H.G. Brittain ed., 1999).*
Kohn EC et al., Clinical Cancer Res 7:1600-1609 (2001); Berlin J et al., J Clin Onc 15: 781-789 (1997); Berlin J et al., Clinical Cancer res 8: 86-94 (2002);.
Bauer KS et al., Clinical Cancer Res 5: 2324-2329 (1999);Yasui H et al., J Biol Chem 45:28762-28770 (1997); Alessandro R et al., J Cell Physiol 215: 111-121 (2008); 6. CDC -Facts About Sodium Azide, 2009.

* cited by examiner

*Primary Examiner* — James O Wilson
*Assistant Examiner* — Alexander R Pagano
(74) *Attorney, Agent, or Firm* — Rashida A Karmali (57) ABSTRACT

New polymorphs of 5-amino or substituted amino 1,2,3-triazole and substituted derivatives thereof, of orotates of the carboxyamidotriazoles, of formulations of the triazoles and orotic acid in the ratio of 1:1 to 1:4 (base:acid) and of safer processes of the preparation of the same are disclosed. The compounds are useful in the control and treatment of diseases including, but not limited to solid cancers, macular degeneration, retinopathy, chronic myeloid leukemia, AIDS and diseases which rely on aberrant signal transduction. The improved processes to prepare the orotate formulations use stable, efficient and safer starting azide intermediate materials in the synthesis of new polymorphs of carboxyamidotriazole.

12 Claims, 6 Drawing Sheets

COMPOSITIONS AND PROCESSES FOR PREPARING 5-AMINO OR SUBSTITUTED AMINO 1,2,3-TRIAZOLES AND TRIAZOLE OROTATE FORMULATIONS

CROSS-REFERENCE TO OTHER APPLICATION

This application is a Continuation-in-part of U.S. patent application Ser. No. 12/584,448 filed on Sep. 4, 2009 now abandoned, which is incorporated herein, with references in its entirety.

FIELD OF INVENTION

This invention is related to new chemical compounds of 5-amino or substituted amino 1,2,3-triazoles as well as substitutes derivatives thereof (referred herein as carboxyamidotriazoles or CAI), to formulations of 5-amino or substituted amino 1,2,3-triazole orotates as well as substituted derivatives thereof, (with defined base:acid ratios, CTOs), to formulations of 5-amino or substituted amino 1,2,3-triazole orotates as well as substituted derivatives thereof and orotic acid, (with defined base:acid ratios, CAOs) and to the safer processes of the preparation of the same, by using stable, more efficient and safer starting materials to synthesize intermediate azide materials necessary in the synthetic pathways for CAI and the orotate formulations —CTO and CAO. More particularly, the invention relates to new polymorphs of 5-amino or substituted amino 1,2,3-triazoles as well as substitutes derivatives thereof. This invention still more particularly relates to novel 5-amino or substituted amino 1,2,3-triazole orotates (CTOs with optimum base:acid ratios in the range 1:1 to 1:4) as well as formulations of 5-amino or substituted amino 1,2,3-triazoles as well as substitutes derivatives thereof and orotic acid (CAO) in optimum base:acid ratios of 1:1 to 1:4, and use of the same in the control and treatment of diseases including, but not limited to solid cancers, macular degeneration, retinopathy, chronic myeloid leukemia, AIDS and diseases which rely on aberrant signal transduction and proliferation.

BACKGROUND TO THE INVENTION

This invention is in the field of development of new polymorphs of 5-amino or substituted amino 1,2,3-triazole (CAI) as well as substituted derivatives thereof, of orotates of 5-amino or substituted amino 1,2,3-triazoles as well as substituted derivatives thereof, and of formulations of 5-amino or substituted amino 1,2,3-triazoles as well as substitutes derivatives thereof and orotic acid (in optimum ratios of base:acid). The objective is to develop new polymorphs of 5-amino or substituted amino 1,2,3-triazoles as well as substitutes derivatives thereof, to improve chemical, biological, pharmacokinetic and toxicokinetic properties and improve therapeutic properties, including, but not limited to anticancer activity, antimetastatic activity, calcium-mediated signal transduction, antiangiogenic, anti-PI3, anti-COX2, apoptosis, down regulation of BCR-ABL protein in chronic myeloid leukemia, regulation of HIV LTR transcription or anti-VEGF1 properties.

In 1986, 5-amino or substituted amino 1,2,3-triazole compounds as well as substituted derivatives thereof were shown to have anticoccidial activity. U.S. Pat. No. 4,590,201, issued to R. J. Bochis et el., 1986, describes the method of preparing 5-amino-1-(4-[4-chlorobenzoyl]-3,5-dichlorobenzyl)-1,2,3-triazole-4 carboxamide (L651582 or CAI) which included use of sodium azide to synthesize one essential intermediate in the pathway, 3,5-dichloro-4-(4-chlorobenzoyl)benzyl azide. Subsequently, L651582 or CAI was shown to inhibit selected signal transduction pathways including those which involve calcium influx, the release of arachidonic acid and the generation of inositol phosphates. U.S. Pat. No. 5,359,078, issued to E. C. Kohn et al, 1994. "L651582" as used herein represents L6515182, CAI, Carboxyamidotriazole, NSC 609974 or 99519-84-3 described in prior art.

U.S. Pat. No. 5,912,346 issued to F. Wehrmann, 1999 then described inorganic and organic salts of L651582, and in particular described the process of preparing the orotate salt of L651582. The L651582 was prepared by the process described in U.S. Pat. No. 4,590,201. The L651582: Orotate was in the ratio of 2:1 (base:acid) as characterized by proton NMR and had a Melting Point of 234-235° C. As described above, the synthesis of the intermediate 3-(4-chlorobenzoyl)-4-chlorobenzyl azide was carried out using the intermediate 3-(4-chlorobenzoyl)-4-chlorobenzyl bromide and sodium azide in ethanol. U.S. Pat. No. 5,912,346 described improved antitumor activity of L651582 Orotate (CAI Orotate, base: acid, 2:1) compared with that of equivalent dose of L651582 in the androgen-independent Dunning R-3227-AT-1 prostate cancer model in rats.

Carboxyamidotriazole, L651582, CAI, NSC 609974, or 99519-84-3, an inhibitor of calcium-mediated signal transduction, is one of the first cytostatic signal inhibitory anticancer drugs discovered. It was tested in patients suffering from solid cancers in Phase I, Phase II and Phase III trials at the National Cancer Institute. However, the NCI stopped the development of L651582 because it failed to demonstrate efficacy in human trials and/or was plagued by poor bioavailability, severe gastrointestinal toxicity, neurotoxicity and problems of tolerability that prevented optimum dosing to achieve therapeutic effect. Capsules of micronized formulation of L651582 in PEG-400 were used in the clinical studies to improve bioavailability of the drug. Kohn E C et al., Clinical Cancer Res 7:1600-1609 (2001); Bauer K S et al., Clinical Cancer Res 5: 2324-2329 (1999); Berlin J et al., J Clin One 15: 781-789 (1997); Berlin J et al., Clinical Cancer res 8: 86-94 (2002); Yasui H et al., J Biol Chem 45:28762-28770 (1997); Alessandro R et al., J Cell Physiol 215: 111-121 (2008).

Therefore, L651582 orotate (base:acid 2:1) described in U.S. Pat. No. 5,912,346, represented a potential way to salvage this promising drug, L651582, by improving its efficacy, based on preclinical studies. However, problems were encountered in the scaling up of the process of preparing L651582 orotate (2:1 ratio) in bulk quantities, according to the method described in U.S. Pat. No. 5,912,346.

858.A1
Step One

With regard to the use of orotic acid in intensifying the analgesic effects of drugs, U.S. Pat. No. 4,061,741, issued to Wawretschek W et al, 1977, describes use of dextropropoxyphene-HCl, laevopropoxyphene-HCl, or sodium salicylate in combination with choline orotate, and concludes that a drug formulation in combination with choline orotate gave the best effects. Clearly, prior art presents contradictory teachings about the proportions and chemical nature of orotic acid bonding with a chemical compounds.

The synthesis scheme described in prior art for L651582 orotate is shown in Reaction Scheme I above. 858 is a product identifier, e.g., 858A to 858D represent intermediates. 858E represents carboxyamidotriazole (CAI). 858F represents carboxyamidotriazole: orotic acid or carboxyamidotriazole:orotate, or CTO as defined herein.

Prior art teachings suggested use of choline orotate in combination with the drug to be a preferred embodiment. Unfortunately, this did not address the problems encountered in the present invention of scaling up the production of CTO for clinical development. It was not clear if the base:acid ratio in L651582 orotate (2:1) was the optimum chemical structure for the drug. Moreover, problems were encountered when scaling up the production of L651582 orotate (2:1) to manufacture large quantities. Few manufacturers had the equipment and facilities required to handle bulk quantities of sodium azide, and those contractors that had the facilities charged large service fees.

After protection of the alcohol group in 3,5-dichlorobenzyl alcohol, as the TBDMS ether step (step 1), the ether is reacted with 4 chlorobenzoyl chloride to form the substituted benzophene (step 2). The benzophene is treated with thionyl chloride (step 3) and then with sodium azide (step 4) to form 3,5-dichloro-4-(4-chlorobenzoyl)benzyl azide. Reaction of this azide with cyanoacetamide produces L651582 (step 5). Reaction of L651582 with orotic acid forms the L651582 orotate (2:1) (step 6).

The use of sodium azide in the above process in step 4 was a serious drawback to scaling up the production of L6515182 orotate in large quantities. Handling of large quantities of sodium azide has to be done in special pressure sensitive reactors since sodium azide is a high energy content hazardous material. The special containment facilities required to handle sodium azide generally increased the cost of manufacture because few drug manufacturers had the capacity to scale up the process to bulk amounts of the drug. This is because sodium azide is a rapidly acting, potentially deadly chemical that exists as an odorless white solid. When mixed with water or an acid, sodium azide changes rapidly to a toxic gas with a pungent odor. It also changes into toxic gas when it comes in contact with solid metals. Survivors of serious sodium azide poisoning may have heart and brain damage and Center for Disease Control and Prevention advises victims to its Hotline immediately. (CDC—Facts About Sodium Azide, 2009). Clearly, there was need to develop a safer, new, affordable and efficient process for the preparation of L651582 orotate without using sodium azide. Competitive bidding at affordable cost was impossible because sodium azide (Step 4) was required in the preparation of 3,5-dichloro-4-(4-chlorobenzoyl)benzyl azide, an intermediate, in the synthetic pathway for L651582 orotate, as shown above. It was therefore necessary to develop an alternate, safer more efficient process to prepare the orotate drug with the optimum chemical configuration and base:acid ratio. The present invention seeks to overcome these drawbacks.

Even though L651582 orotate was demonstrated to have significantly higher antitumor activity in the prostatic cancer rat model (U.S. Pat. No. 5,912,346) there was no teaching or suggestion regarding whether the chemical, pharmacological and biological properties of L651582 orotate in the base:acid ratio of 2:1 were optimum or not. Clearly, there is need to develop new polymorphs of CAI and an orotate compound of CAI that offers optimum chemical, biological, pharmacological, therapeutic and toxicokinetic characteristics to justify clinical development.

Thus, the primary objective of the invention was to develop an orotate formulation of CAI (wherein the base:acid ratio is in the range of 1:1 to 1:4) having improved effectiveness which is related to its bioavailability, which in turn is dependent on its solubility in human body fluids.

Another objective of the invention was to develop a safer, more cost effective process to produce bulk quantities of CAI, CTO (as orotate of CAI) and CAO (as formulation of CAI mixed with orotic acid).

An important objective of the invention was to make a safer CAI by using safer and less toxic ingredients to produce intermediates instead of using sodium azide or potassium azide which are highly toxic at very low concentrations. CAI produced by the processes described in prior art had been found to cause serious neurotoxicity and gastric toxicities in patients. Therefore, it was important to use of safer ingredients and an improved process to produce has also resulted in production of new polymorphs of CAI and its orotate formulations.

The pertinent subject matter of the above references is specifically incorporated herein by reference, in their entirety.

SUMMARY OF THE INVENTION

The present invention seeks to overcome drawbacks inherent in the prior art by providing compositions of new polymorphs of 5-amino or substituted amino 1,2,3-triazole as well as substituted derivatives thereof (referred herein as carboxyamidotriazoles or CAI); to formulations of 5-amino or substituted amino 1,2,3-triazole orotates as well as substituted derivatives thereof, (with defined base:acid ratios, CTOs); and to formulations of 5-amino or substituted amino 1,2,3-triazole orotates as well as substituted derivatives thereof and orotic acid, (with defined base:acid ratios, CAOs).

The present invention provides safer processes of the preparation of the same, by using stable, more efficient and safer starting materials to synthesize intermediate azide materials necessary in the synthetic pathways for CAI and the orotate formulations —CTO and CAO.

More particularly, the invention relates to new polymorphs of 5-amino or substituted amino 1,2,3-triazoles (CAI) as well as substitutes derivatives thereof. CAI is present in several polymorphic forms, including, but not limited to Form 1 or Form 2.

This invention still more particularly relates to novel 5-amino or substituted amino 1,2,3-triazole orotates (CTOs with optimum base:acid ratios in the range 1:1 to 1:4) as well as formulations of 5-amino or substituted amino 1,2,3-triazoles as well as substitutes derivatives thereof and orotic acid (CAO) in optimum base:acid ratios, orotates (CTOs) as well as substituted derivatives thereof.

In another aspect, the invention relates to a process for preparing the intermediate azide materials necessary in the synthetic pathways by using a stable, safer and affordable starting materials, including but not limited to diphenylphosphoryl azide or trimethyl silyl azide, $TMSN_3$, instead of sodium azide or potassium azide.

More particularly, this invention relates to novel polymorphs of 5-amino or substituted amino 1,2,3-triazole as well as substituted derivatives thereof, their orotate derivatives (CTO) (base:acid ratio in the range of 1:1 to 1:4) and use of the same in the treatment of diseases including, but not limited to solid cancers, macular degeneration, retinopathy, chronic myeloid leukemia, AIDS and diseases which rely on aberrant signal transduction and proliferation pathways such as voltage-independent calcium channel blocker, PI3, COX2, BCR-ABL, apoptosis, HIV LTR transcription or VEGF1.

In view of the foregoing state of the art, the present invention provides orotate derivatives of novel 5-amino or substituted amino 1,2,3-triazole or carboxyamidotriazole orotates (CTO) containing therein a chemical organic moiety that increases their bioavailability, delivery to the target, antitumor efficacy and reduces toxicity. Specifically, one class of carboxyamidotriazole orotates (CTOs) having an ionic bonding in the ratio of in the range of about 1:1 to 1:4 (triazole:orotic acid) constitute the new compounds of the invention.

In addition, formulations of 5-amino or substituted amino 1,2,3-triazole (CAI) as well as substituted derivatives thereof, and orotic acid, (with defined base:acid ratios, 1:1 to 1:4, CAOs)

In another aspect, the invention provides a process for the preparation of the azide intermediate 3,5-dichloro-4-(4-chlorobenzoyl)benzyl azide without using sodium azide, but instead using diphenylphosphoryl azide (DPPA) or $TMN_3$ or safer azide equivalents. DPPA is significantly safer than sodium azide and has been used to convert alcohols directly to azides, and therefore, eliminates a step (step 3 in the Scheme outlined above) in the synthetic pathway for CTO.

Another objective of the invention is to increase the bioavailability of CTO when given orally or by other routes, in human and other mammals and improving the delivery of CTO to the target, for example, by improving absorption, delivery and transport through tissues, the blood brain barrier and the choroid retina complex.

Yet another object of the invention is to reduce toxicity of CTO and related compounds when administered as orotate salts by increasing the clearance of the drug from the blood, tissues and organs.

The invention can further be used to reduce drug interactions and side effects when the CTO or CAI in combination with orotic acid (CAO) are administered as formulations.

Another objective of the invention is to provide compositions of CTO for treating human neoplasms, and particularly, primary or metastatic tumors, diseases involving neovascularization such as macular degeneration, retinopathy, diabetic retinopathy, chronic myeloid leukemia, AIDS and diseases which rely on aberrant signal transduction and proliferation pathways such as voltage-independent calcium channel blocker, PI3, COX2, BCR-ABL, apoptosis, HIV LTR transcription or VEGF1, and reducing the toxic secondary effects of the drug by reducing the levels of the drug in noncancerous tissues that are susceptible targets of drug toxicity, by 10% to 100% when compared with giving L651582 or CAI.

A preferred embodiment of the invention comprises CTO in the ratio of 1:1, base:acid, a more preferred embodiment in the ratio 1:2 and a most preferred embodiment of the invention comprises compositions of CTO (in the ratio of about 0.7:1.3) prepared by the new process of the invention, for treatment of diseases including, but not limited to solid cancers, macular degeneration, retinopathy, chronic myeloid leukemia and modulation of signal transduction pathways, such as PI3, COX2, BCR-ABL, STATS, CrkL, apoptosis, HIV LTR transcription, VEGF1 or others.

DETAILED DESCRIPTION OF THE INVENTION

The present invention provides novel polymorphs of 5-amino or a substituted amino 1,2,3-triazole or their substituted amino 1,2,3-triazoles (CAI) prepared by a novel process and include a class of compounds of the formula I. The novel polymorphs of CAI include, but are not limited to Form 1 or Form 2 as characterized by techniques such as NMR, DSC, FT-IR and XRDP.

Formula I in which $R_1$ has the formula II, wherein, wherein p is 0 to 2; m is 0 to 4; and n is 0 to 5; X is O, S, SO, $SO_2$, CO, CHCN, $CH_2$ or $C=NR_6$ where $R_6$ is hydrogen, lower alkyl, hydroxy, lower alkoxy, amino, lower alkylamino, dilower alkyl amino or cyano; and, $R_4$ and $R_5$ are independently halogen (F, Cl, Br), cyano, trifluoromethyl, lower alkanoyl, nitro, lower alkyl, lower alkoxy, carboxy, lower carbalkoxy, trifluoromethoxy, acetamido, lower alkylthio, lower alkylsulfinyl, lower alkylsulfonyl, trichlorovinyl, trifluoromethylthio, trifluoromethylsulfinyl, or trifluoromethylsulfonyl; $R_2$ is amino, mono or dilower alkyl amino, acetamido, acetimido, ureido, formamido, formimido or guanidino; and $R_3$ is carbamoyl, cyano, carbazoyl, amidino or N-hydroxycarbamoyl; wherein the lower alkyl, lower alkyl containing, lower alkoxy and lower alkanoyl groups contain from 1 to 3 carbon atoms.

The 5-amino or a substituted amino 1,2,3-triazole compound is reacted with orotic acid, to form orotate compounds of 5-amino or a substituted amino 1,2,3-triazole compound in the ratio in the range of 1:1 to 1:4 (base:acid) by the improved and safer process of the invention to form CTOs for use according to the methods of the present invention.

The novel polymorphs of CAI are further reacted with orotic acid to form orotate compounds of a class of compounds of the formula II:

Formula II in which orotic acid is ionically bonded to R2, wherein p is 0 to 2; m is 0 to 4; and n is 0 to 5; X is O, S, SO, $SO_2$, CO, CHCN, $CH_2$ or $C=NR_6$ where $R_6$ is hydrogen, lower alkyl, hydroxy, lower alkoxy, amino, lower alkylamino, dilower alkyl amino or cyano; and, $R_4$ and $R_5$ are independently halogen (F, Cl, Br), cyano, trifluoromethyl, lower alkanoyl, nitro, lower alkyl, lower alkoxy, carboxy, lower carbalkoxy, trifluoromethoxy, acetamido, lower alkylthio, lower alkylsulfinyl, lower alkylsulfonyl, trichlorovinyl, trifluoromethylthio, trifluoromethylsulfinyl, or trifluoromethylsulfonyl; $R_2$ is amino, mono or dilower alkyl amino, acetamido, acetimido, ureido, formamido, formimido or guanidino; and $R_3$ is carbamoyl, cyano, carbazoyl, amidino or N-hydroxycarbamoyl; wherein the lower alkyl, lower alkyl containing, lower alkoxy and lower alkanoyl groups contain from 1 to 3 carbon atoms.

Figure 1:
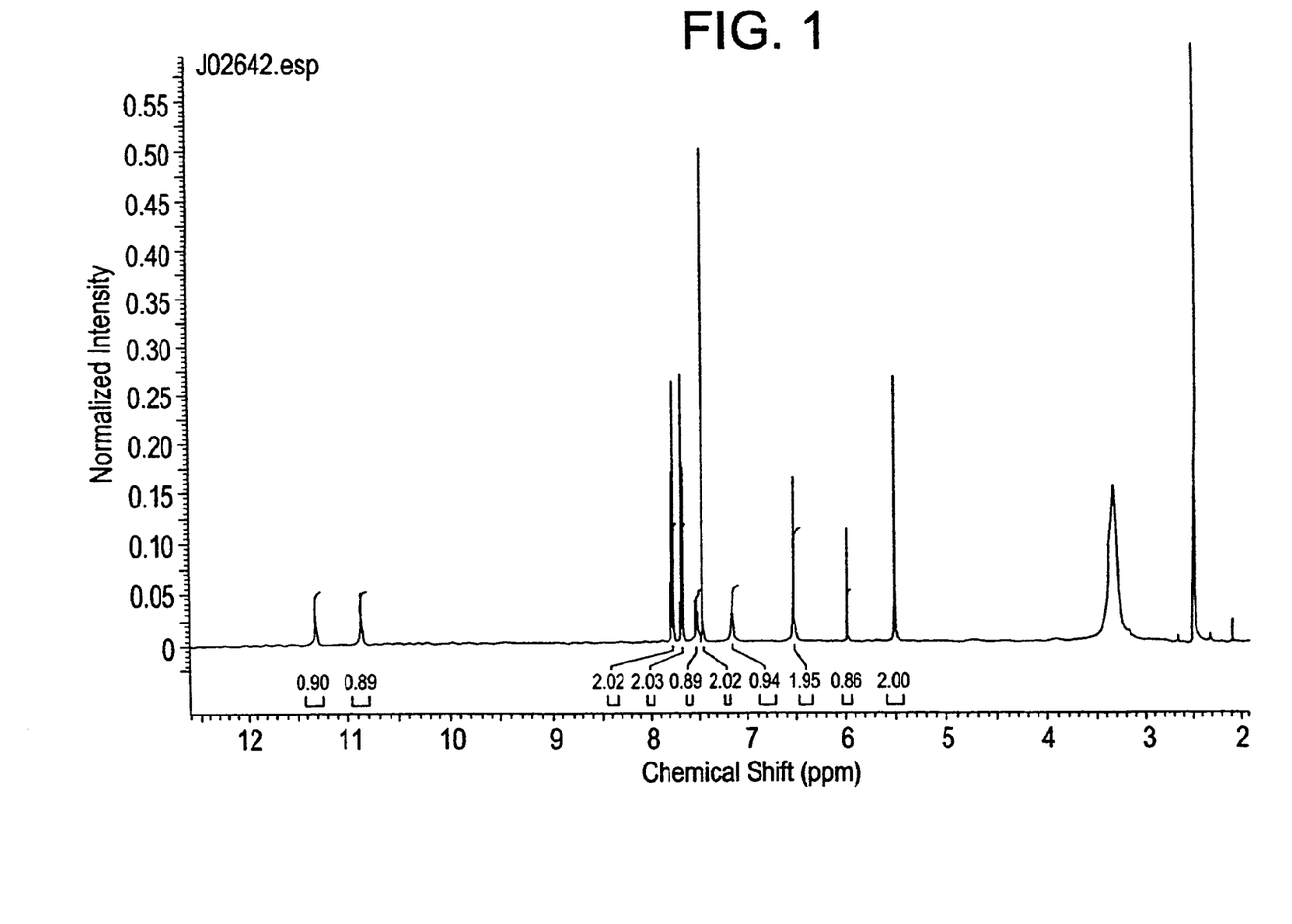
FIG. 1 illustrates the structure of CTO by NMR as CAI: Orotic Acid or CAI:Orotate, of a CTO sample J02642 having a Form 1 or Pattern 1 polymorph of CAI.
Figure 2:
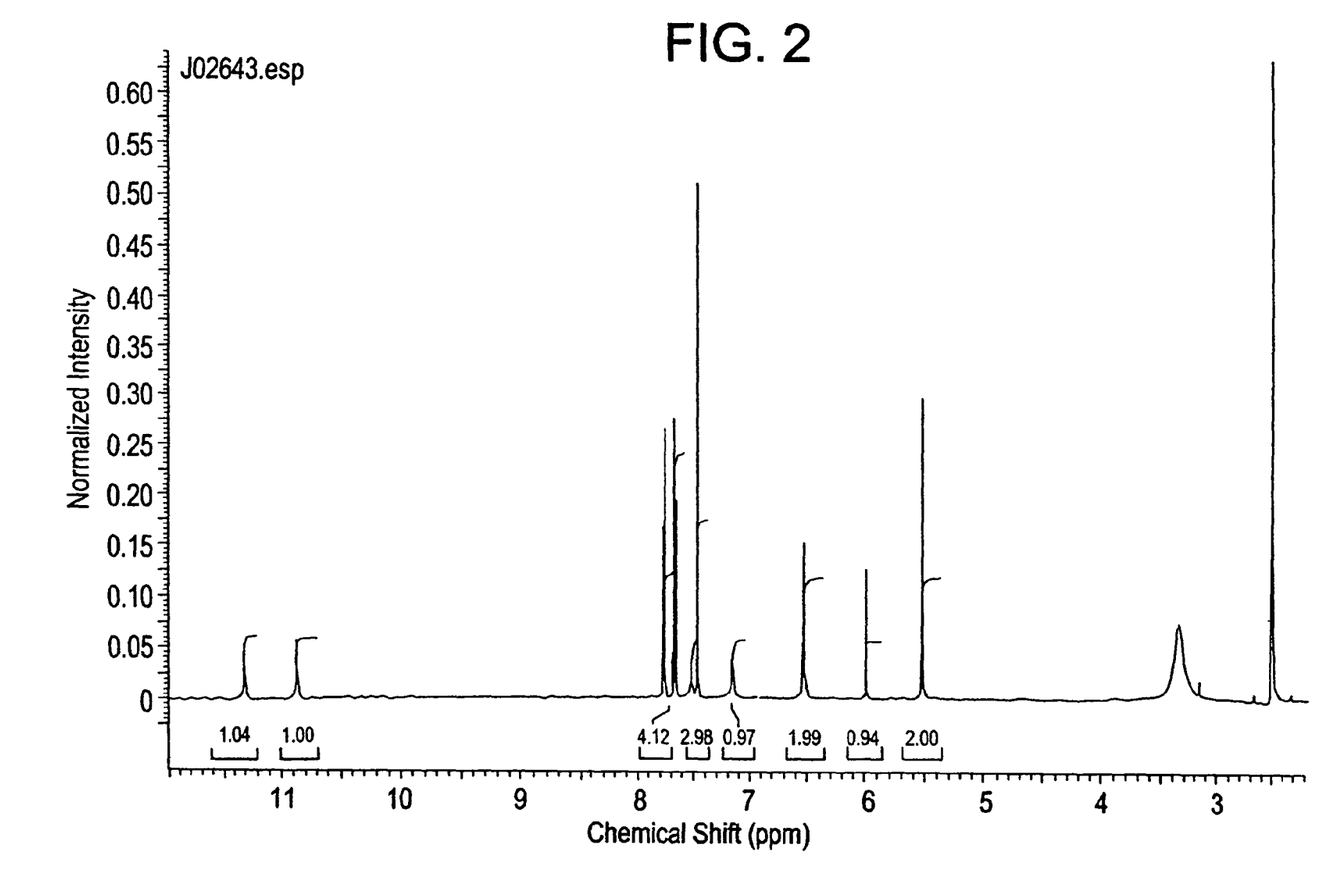
FIG. 2 illustrates the structure of CTO by NMR as CAI: Orotic Acid or CAI:Orotate, of a CTO sample 102643 having a Form 2 or Pattern 2 polymorph of CAI.
Figure 3:
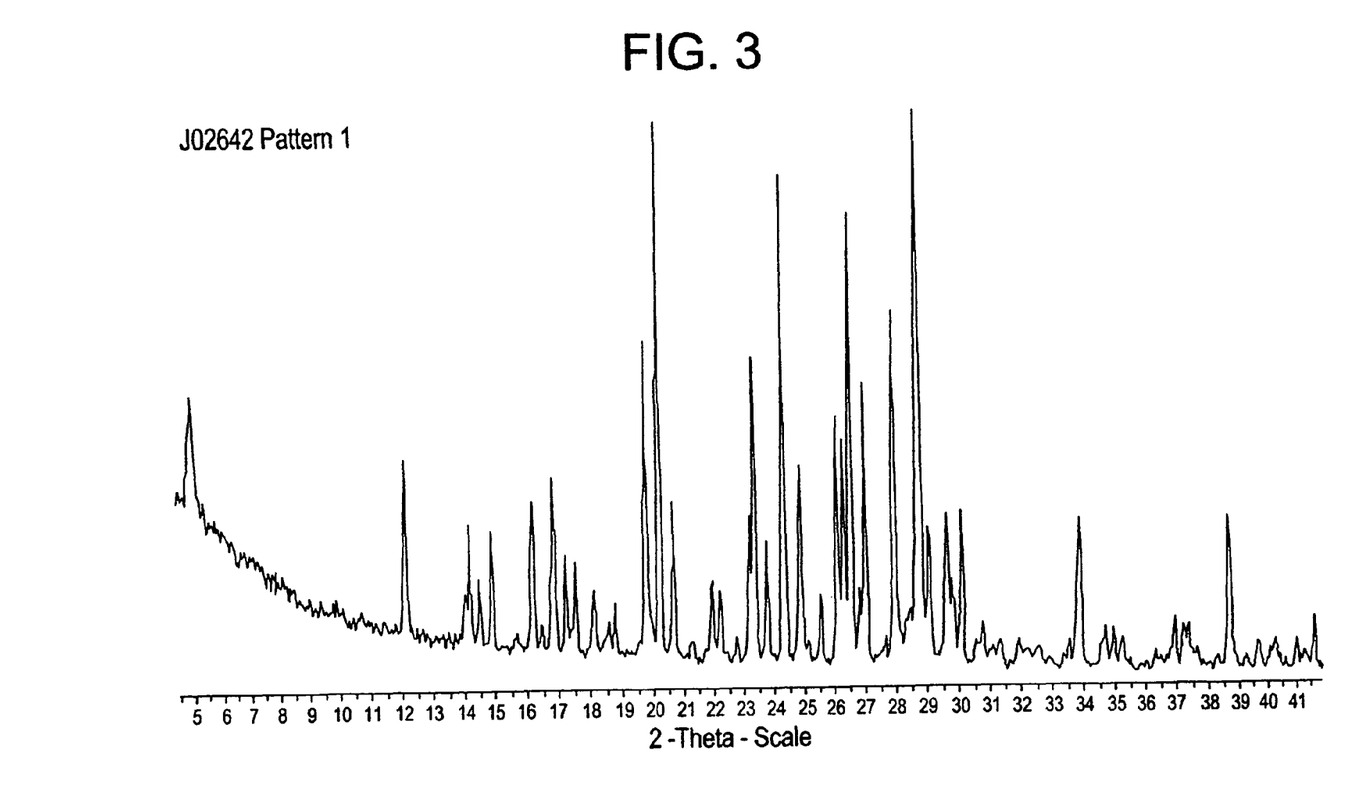
FIG. 3 illustrates a High resolution diffractogram of CTO sample J02642 having Form 1 or Pattern 1 polymorph of CAI.
Figure 4:
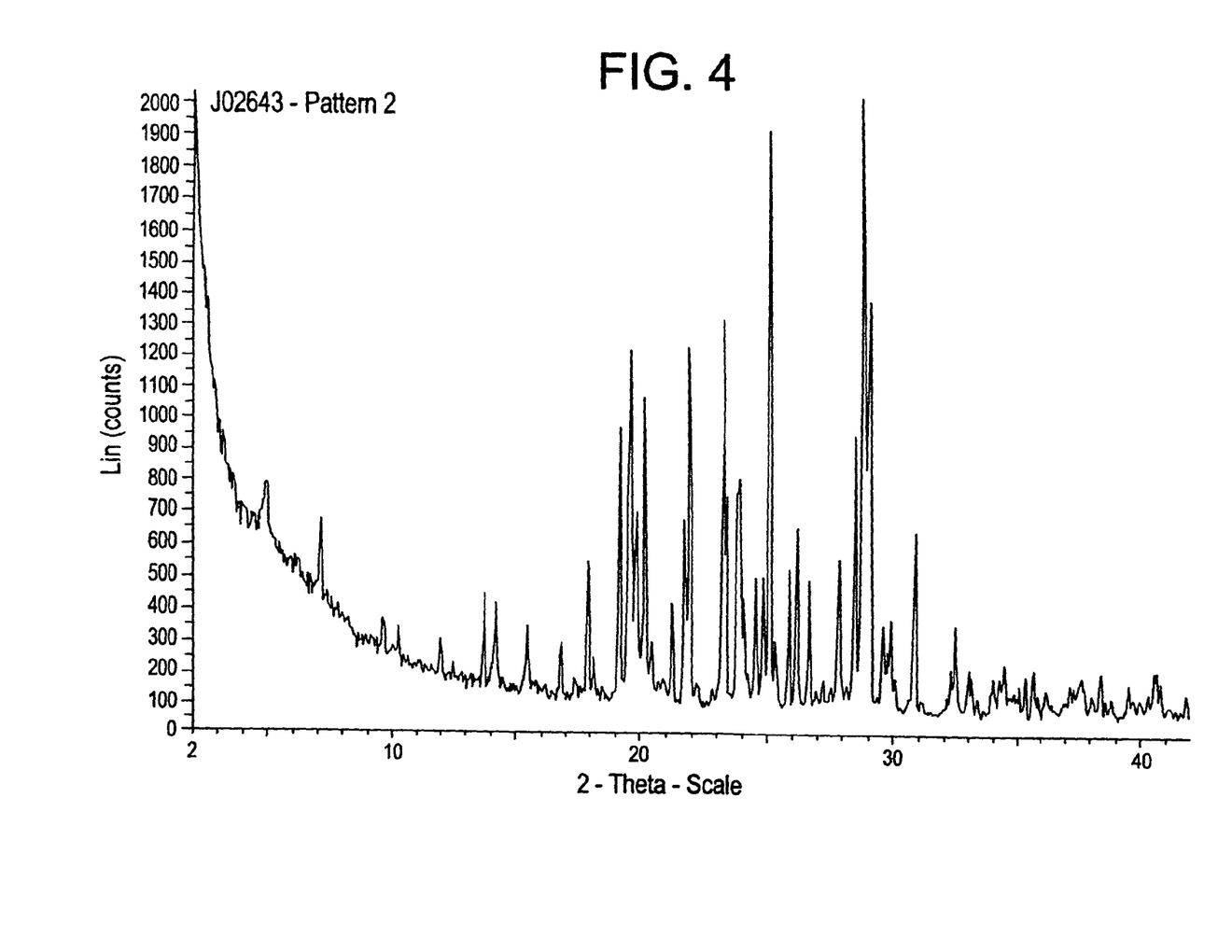
FIG. 4 illustrates a High resolution diffractogram of CTO sample J02643 having Form 2 or Pattern 2 polymorph of CAI.
Figure 5:
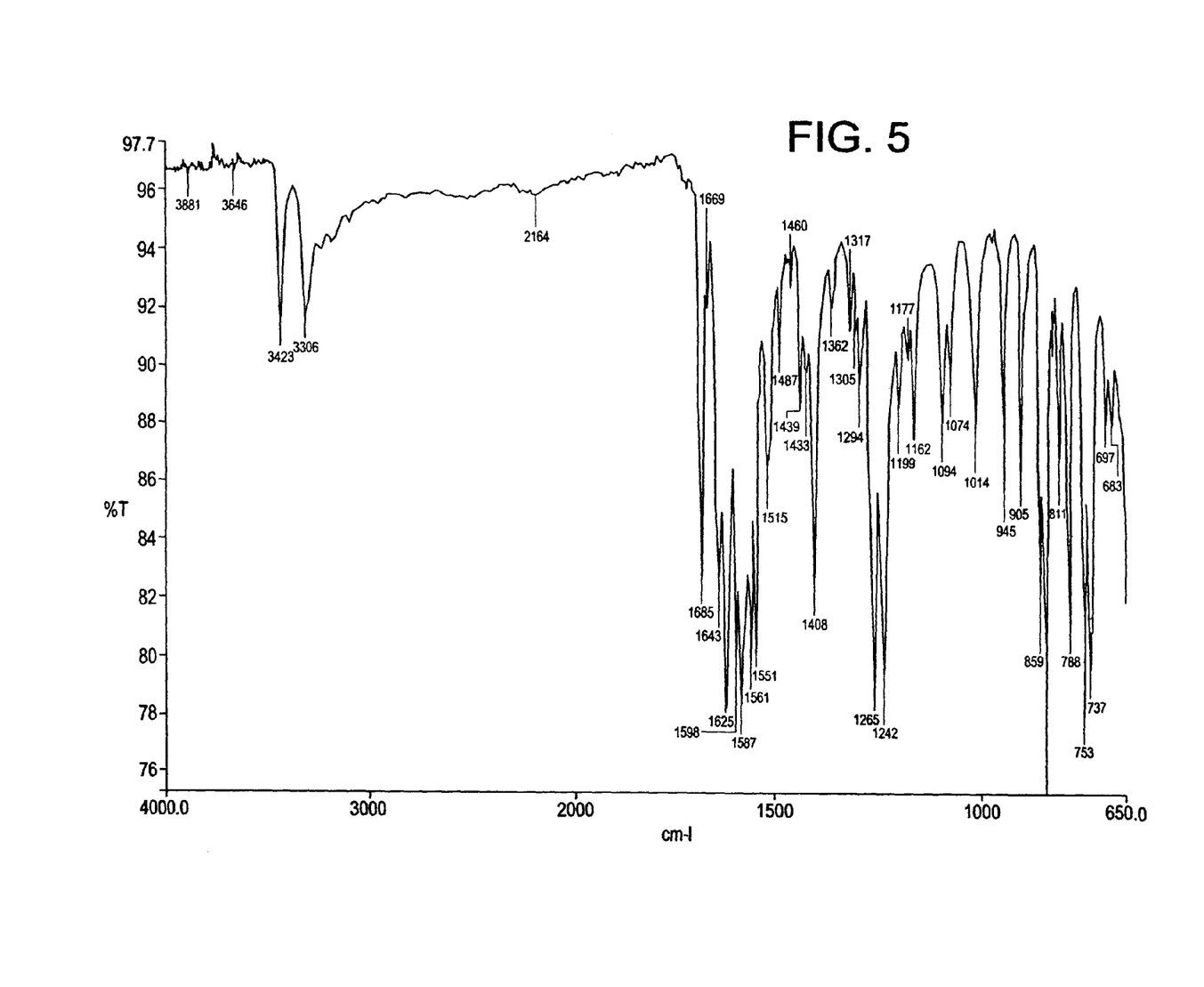
FIG. 5 illustrates the FT-IR of CTO sample J02642 having Form 1 or Pattern 1 polymorph of CAI.
Figure 6:
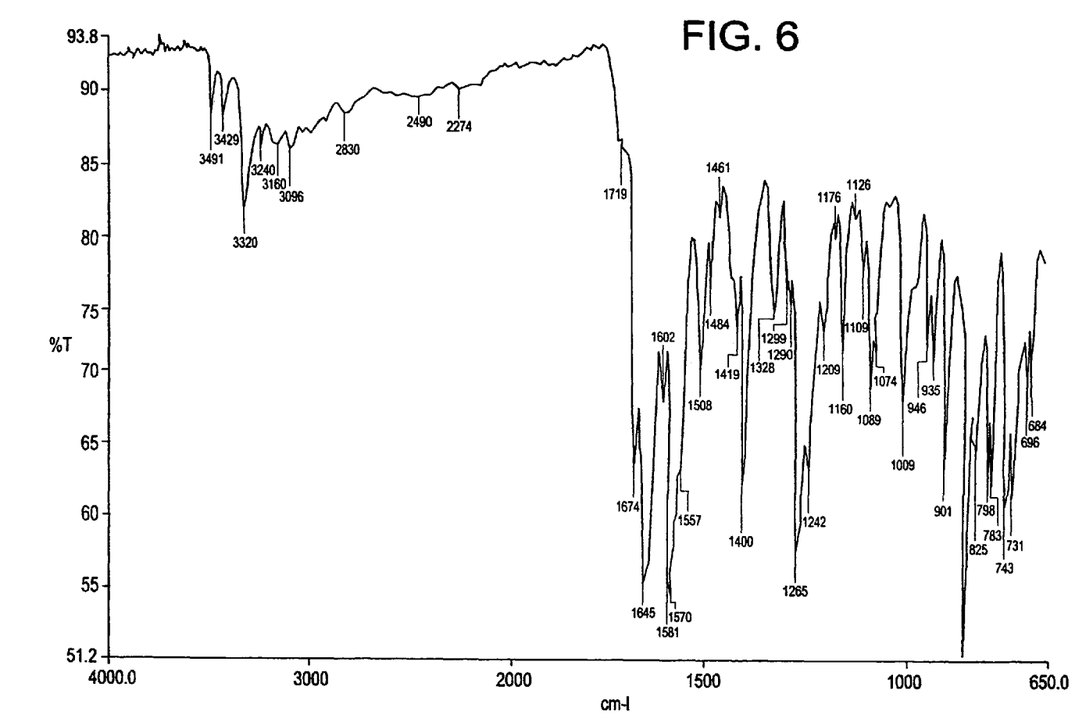
FIG. 6 illustrates the FT-IR of CTO sample J02643 having Form 2 or Pattern 2 polymorph of CAI.

The preferred embodiments of "CTO" as defined herein, has the empirical formula of $C_{22}H_{16}Cl_3N_7O_6$, molecular weight of 580.76. two transition Melting Points at 201° C. and 236° C. CTO includes new polymorphs of CAI ionically bonded orotic acid. CAI has many polymorphs, including, but not limited to Form 1 (Pattern 1) or Form 2 (Pattern 2). The two embodiments of CTO have different transition melting points, for example, CTO (Form 1, Pattern 1) has Melting Points at about 136° C., 194° C. and 235° C.; and CTO (Form 2, Pattern 2) has Melting Points at about 137° C. and 234° C. The two embodiments of CTO have a $^1H$ NMR spectrum consistent with the structure CAI:Orotic Acid (FIG. 1 and FIG. 2, respectively) and FT-IR patterns consistent with Form 1 and Form 2 (FIG. 3 and FIG. 4, respectively). CTO is crystalline as shown by x-ray powder diffraction patterns for Form 1 and Form 2 (FIG. 5 and FIG. 6 respectively).

Chemical names of the preferred embodiment of CTO include:
  5-amino-1-(4-(4-chlorobenzoyl)-3,5-dichlorobenzyl)-1,2,3-triazole-4-carboxamide, compound with orotic acid;
  5-amino-1-(3,5-dichloro-4-(4-chlorobenzoyl)benzyl)-1H-1,2,3-triazole-4-carboxamide, compound with orotic acid; and 5-Amino-1-{[3,5-dichloro-4-(4-chlorobenzoyl)phenyl]methyl}-1H,1,2,3-triazole-4-carboxamide, compound with orotic acid.

More particularly, the chemical structure of the polymorphs of CTO is:

CAI: orotic acid

An additional embodiment includes the formulation of different polymorphs of CAI and Orotic acid (CAO). The new polymorphs of 5-amino or a substituted amino 1,2,3-triazole (CAI) or 5-amino or substituted amino 1,2,3-triazoles are mixed with ortic acid in the range of 1:1 to 1:4 (base:acid) to provide formulations of CAO use according to the methods of the present invention.

New Process:

The novel process of the invention wherein compounds of the invention can be prepared is shown in Reaction Scheme II below in five (5) steps. More specifically, the novel process uses diphenylphosphoryl azide to react with intermediate 858.B in step 3 instead of with sodium azide. It eliminates step 3 in prior art to form intermediate 858.C. See Scheme I above (six steps). The detailed processes are described in the Examples. 858.A through 858.F represents intermediate products and CTO as summarized below:

858.A represents t-Butyldimethylsilyl-3,5-dichlorobenzyl ether.

858.B represents 3,5-dichloro-4-(4-chlorobenzoyl)benzyl alcohol.

858.C represents 3,5-dichloro-4-(4'-chlorobenzoyl)benzyl chloride.

858.D represents 3,5-dichloro-4-(4'-chlorobenzoyl)benzyl azide.

858.E represents 5-Amino-1-(4-(4-chlorobenzoyl)-3,5-dichlorobenzyl)-1,2,3-triazole-4-carboxamide.

858.F represents 5-Amino-1-(4-(4-chlorobenzoyl)-3,5-dichlorobenzyl)-1,2,3-triazole-4-carboxamide, compound with orotic acid, (CAI:Orotic acid) (CAI:Orotate) (CTO).

Importantly, it has been observed that different polymorphs of CAI, CTO and CAO manufactured by the above process exhibit less gastric lesions and toxicity in rodents when compared with CAI which was synthesized by procedures described in prior art. This may be related to the absence of use of toxic ingredients such as sodium azide or potassium azide.

The new process has also resulted in the production of new polymorphs of CAI, CTO and CAO. Thus, compounds of the invention include molecules that crystallize into more that one different crystal structure and exhibit different chemical properties of different polymorphs of CAI as characterized by techniques such as NMR, DSC, FT-IR and XRDP (FIGS. 1 to 6).

Dosage and Formulation 5-amino or substituted amino 1,2,3-triazoles as well as substitute derivatives thereof been manufactured into different polymorphs having chemical and biological properties that have overcome the disadvantages of CAI produced by procedures described in prior art.

In addition, 5-amino or substituted amino 1,2,3-triazole as well as substitute derivatives have been chemically reacted with orotic acid to form orotates (CTO) in the ratio 1:1 to 1:4 (base:acid, having unique bioavailability, pharmacokinetic properties, safety and effectiveness.

An alternate embodiment includes polymorphs of 5-amino or substituted amino 1,2,3-triazoles as well as substitute derivatives thereof, mixed with orotic acid, in the ratio 1:1 to 1:4 (base:acid) to form formulations of CAI and orotic acid (CAO).

The above pharmaceutical compositions and formulations may be formulated into pharmaceutical preparations for administration to mammals for prevention and treatment of primary and metastatic neoplasms, chronic myeloid leukemia, macular degeneration, retinopathies and other cell proliferative diseases. Many of the triazole orotate compounds may be provided as organic acid salts directly or with pharmaceutically compatible counterions, a form in which they are merely water-soluble. Salts tend to be more soluble in aqueous or other protonic solvents than are the corresponding free base forms. The therapeutic compounds or pharmaceutical compositions may be administered intravenously, intraperitoneally, subcutaneously, intramuscularly, intrathecally, orally, rectally, topically, or by aerosol.

Formulations suitable for oral administration include solid powder formulations, liquid solutions of the active compound dissolved in diluents such as saline, water or PEG 400; capsules or tablets, each containing a predetermined amount of the active agent as solid, powder, granules or gelatin; suspensions in an approximate medium; and emulsions.

Formulations suitable for parenteral administration include aqueous and non-aqueous isotonic sterile solutions, which contain buffers, antioxidants and preservatives. The formulations may be in unit dose or multi-dose sealed containers.

Patient dosages for oral administration of CTO range from 0.25-500 mg/day, commonly 25-100 mg/day, and typically from 50-400 mg/day. Stated in terms of patient body weight, usual dosage range from 0.005 to 10 mg/kg/day, commonly from 0.5-2.0 mg/kg/day, typically from 1.0 to 8.0 mg/kg/day. Stated in terms of patient body surface areas, usual dosage range from 0.1-300 mg/m$^2$/day, commonly from 20-250 mg/m$^2$/day, typically from 25-50 mg/m$^2$/day. Dosage amount and interval may be adjusted individually to provide plasma levels of the active moiety which are sufficient to maintain the anti-proliferative, anti-metastatic effects, antiangiogenic effects or other therapeutic effects in diseases which rely on aberrant signal transduction and proliferation.

Doses may be adjusted depending on the route of administration, for example for intravenous, for inhalation/aerosol, for direct intraperitoneal or subcutaneous, for topical or for intrathecal administrations.

A variety of delivery systems for the pharmacological compounds may be employed, including, but not limited to, liposomes, nanoparticles, suspensions and emulsions. The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Furthermore, one may administer the drug in a targeted drug delivery system, for example, in a liposome coated with tumor-specific antibody, as nanoparticles and other forms. The liposomes or nanoparticles may be targeted to and taken up selectively by the tumor or other disease target.

One of the most difficult properties to build into a newly discovered lead molecule is the desired pharmacokinetic profile, particularly in the case of orally dosed compounds. "Most experienced medicinal chemists would prefer to start in a structural series that has inherently good pharmacokinetic properties, albeit with poor potency on the target receptor, and then set about improving the potency on the target, rather than working in the other direction", "Organic Chemistry in Drug Discovery, Drug Discovery", Science 303: 1810-1813 (2004).

Improving the Bioavailability of CTO Administered Orally.

The present invention relates generally to the method of increasing the oral bioavailability, delivery and clearance of CTO, a unique orotate of L651582 in the ratio 1:1: to 1:4 (base:acid). The present invention provides processes to prepare orotate salts of water-insoluble drugs having an ionizable center, to improve the drugs' oral bioavailability, toxicology profile and efficacy. Preferably the CTO is in the ratio 1:1 and more preferably it is in the ratio 1:2 and most preferably it is in the ratio 0.7:1.3.

The absorption of drugs via the oral route is a subject of intense investigation in the pharmaceutical industry since good bioavailability implies that the drug is able to reach the systemic circulation by mouth. Oral absorption is affected by both the drug properties and the physiology of the gastrointestinal tract, including drug dissolution from the dosage form, the manner in which the drug interacts with the aqueous environment and membrane, permeation across the membrane and irreversible removal by first-pass organs such as the intestine, liver and lung. Some pharmaceutical agents that exhibit low-solubility show poor bioavailability or irregular absorption, the degree of irregularity being affected by factors such as dose level, fed state of the patient, and physicochemical properties of the drug.

The majority of drug absorption occurs at the small intestine because of the large surface area since the presence of the villi and microvilli increases the absorptive area manifold. The circulation of the intestine is unique in that the intestine is the anterior or portal tissue that regulates the flow of substrates to the liver. The intestinal venous blood constitutes about 75% of the blood supply to the liver. Therefore, for drugs that are highly cleared by the intestine, the contribution of the liver, kidney or lung to drug metabolism will become reduced. Conversely, for drugs that are poorly extracted by the intestine, the substrate is able to reach the next organs, the liver and the lung for removal. Therefore, the concentration of drug entering the intestine and the intestinal flow rate alter the rate of drug delivery and affect the rates of intestinal and clearance through hepatic first-pass metabolism.

"Drug bioavailability" is defined here as the amount of drug systemically available over time. The present invention increases drug bioavailability of pharmaceutical agents by converting them into orotate salts. This may be achieved by altering the hydrophilic and lipophilic properties of the drug so that the drug permeates the membrane wall and blood perfusion rate becomes the overall rate-limiting step for absorption, or by inhibiting drug biotransformation in the gut and/or by inhibiting active back transport systems in the gut that decrease the net transport of drugs across the gut membrane into the blood stream. In either case, the composition responsible for increased drug bioavailability is the orotate salt of the pharmaceutical agent. For reasons that are not immediately apparent, it has been discovered that conversion of a water-insoluble L651582 into CTO (base:acid, 0.5:1 to 1:2) provides a method for increasing the bioavailability of an orally administered pharmaceutical agent to a mammal in need of treatment.

Changes in the integrated systemic concentrations overtime are indicated by area under the curve (AUC) or $C_{max}$, both parameters well known in the art.

The present invention provides methods wherein a composition provides an increase in bioavailability of the orotate salt of the pharmaceutical agent as measured by AUC of at least 25% to 100% relative to dosing of the pharmaceutical agent.

The invention provides a composition that increases the bioavailability of the orotate salt of the pharmaceutical agent as measured by Cmax of at least 50% to 100%

"Side effects" or "toxicity" or "adverse drug reactions" of chemotherapeutic agents are observed in the acute phase of chemotherapy administration and in patients cured of the cancer with subclinical tissue damage. There is a higher recognition of drug-related tissue side effects which may be quite severe, disabling and irreversible. The clinician must be aware of the potential tissue/organ complications of chemotherapeutic agents and where appropriate perform a baseline tissue examination before initiating the therapy.

"Clearance" of drug occurs by perfusion of blood to the organs of extraction. "Extraction" refers to the proportion of drug presented to the organ which is removed irreversibly (excreted) or altered to a different chemical form (metabolism).

The present invention provides a method to increase clearance of the orotate derivatives of CTO from noncancerous or normal tissues as measured by pharmacological studies at least 25% to 100% relative to dosing of the pharmaceutical agent.

"Bioavailability" of a drug following oral dosing is the extent to which or rate at which the active moiety of the drug or metabolite enters systemic circulation, thereby gaining access to the site of action. The physiochemical properties of a drug govern its absorptive potential, and binding to serum proteins. The efficacy of the drug depends on its interaction with the molecular target. Therefore, the properties of the dosage form which partly depend on its chemical characteristics and on processes for manufacture of the drug in bulk quantities. Differences in bioavailability, efficacy, transport and clearance among chemical formulations of a given drug can have clinical significance.

"Absorption" rate is important because even when a drug is absorbed completely, it may be absorbed too slowly to produce a therapeutic blood level quickly enough or so rapidly that toxicity results from high drug concentrations given to achieve the therapeutic level after each dose. Absorption occurs by one of three methods, either passive diffusion, active transport or facilitated active transport. Passive diffusion is simply the passage of molecules across the mucosal barrier until the concentration of molecules reaches osmotic balance on both sides of the membrane. In active transport the molecule is actively pumped across the mucosa. In facilitated transport, a carrier generally a protein, is required to convey the molecule across the membrane for absorption. The present invention provides CTO compounds in chemical configurations that permit the drug to be delivered successfully to different tissues and organs and even cross the blood brain barrier, to reach the brain.

Orotic acid, a free pyrimidine is important in the synthesis of uridylate (UPP) a major pyrimidine nucleotide. Pyrimidines play a central role in cellular regulation and metabolism. They are substrates for DNA/RNA biosynthesis, regulators of the biosynthesis of some amino acids, and cofactors in the biosynthesis of phospholipids, glycolipids, sugars and polysaccharides. The classical de novo pyrimidine biosynthetic pathway ends with the synthesis of UMP. Biochemistry, ed. Lubert Stryer, ed, W.H. Freeman & Co NY, $4^{th}$ ed, 739-762 (1995). The present invention provides a class of CTOs that undergo dissolution to release the drug as a charged molecule and free orotic acid, which may prevent binding of the drug to proteins and facilitate transport to the target and rapid clearance.

The invention provides embodiments showing increase in effectiveness of the CTO as measured by improvement in 1) efficacy of CTO compared with formulation of equivalent dose of CAI+orotic acid, 2) bioavailability and clearance of CTO when given as encapsulated solid CTO compared to CTO in PEG-400, 3) transport of orally administered CTO to the brain through the blood brain barrier, 4) transport of orally administered CTO to different eye tissues, including the choroid-retina complex and vitreous humor in dogs.

Importantly, the preclinical toxicity of CTO was determined in dogs by the PO route at 175, 350, 1025 mg/kg/day and no deaths occurred after 28 days.

EXAMPLES

Example 1

4-Chlorobenzoyl Chloride 3,5-Dichlorobenzyl alcohol (1 mole) is treated with tert-butyldimethylsilyl chloride (1.05 mole), Imidazole, 99% (2.44 mole), 4-Dimethylaminopyridine in N,N-Dimethylformamide at cold temperature to produce t-Butyldimethylsilyl-3,5-dichlorobenzyl ether (858.A1) at the extraction work-up.

Example 2

3,5-Dichloro-4-(4-chlorobenzoyl)benzyl alcohol

React t-Butyldimethylsilyl-3,5-dichlorobenzyl ether (858.A1) (1 mole) with n-Butyllithium 1.6M solution in hexane followed by 4-Chlorobenzoyl chloride, (1.01 mole), in Tetrahydrofuran, while cold and treat the intermediate with aqueous Hydrochloric acid to give 3,5-dichloro-4-(4-chlorobenzoyl)benzyl alcohol (858.B).

Example 3

3,5-dichloro-4-(4-chlorobenzoyl)benzyl azide 3,5-dichloro-4-(4-chlorobenzoyl)benzyl alcohol (858.B) (1 mole) is reacted with diphenylphosphoryl azide (diphenylphosphonic azide) (DPPA) (1.2 mole, and 1,8-Diazabicyclo[5.4.0]undec-7-ene, (Synonym: DBU) (1.2 mole)) in toluene at cold temperature, followed by aqueous work-up and alcohol titration, to give 3,5-dichloro-4-(4'-chlorobenzoyl) benzyl azide (858.D). DPPA is an organic compound that is used in the synthesis of other organic compounds. Aust. J. Chem 26:1591-1593 (1973). The stability of DPPA towards heating is shown by its distillation at 157° C. and by the fact that vigorous evolution of nitrogen is not observed until a temperature of 175° C. is reached.

Example 4

5-Amino-1-(4-(4-chlorobenzoyl)-3,5-dichlorobenzyl)-1,2,3-triazole-4-carboxamide (CAI)

3,5-dichloro-4-(4'-chlorobenzoyl)benzyl azide (858.D) (1 mole) is reacted with cyanoacetamide (1.69 mole) in hot Acetonitrile, and Potassium carbonate, (6.2 mole) to give 5-amino-1-(4-(4-chlorobenzoyl)-3,5-dichlorobenzyl)-1,2,3-triazole-4-carboxamide (858.E).

Example 5

5-Amino-1-(4-(4-chlorobenzoyl)-3,5-dichlorobenzyl)-1,2,3-triazole-4-carboxamide, compound with orotic acid, (CAI:Orotic acid)

5-amino-1-(4-(4-chlorobenzoyl)-3,5-dichlorobenzyl)-1,2,3-triazole-4-carboxamide (858.E) (1 mole) is reacted with orotic acid (1.03 mole) and methanol/water mixture to give 5-Amino-1-(4-(4-chlorobenzoyl)-3,5-dichlorobenzyl)-1,2,3-triazole-4-carboxamide, solid compound with orotic acid, (CAI:Orotic acid; 1:1) (CTO) (858.F), MW 580.76 g, having transitional melting points of about 151° C., 238° C. and 332° C., measured by differential scanning calorimetry. The XRPD pattern indicates that the CTO is composed of crystalline and amorphous (polymorphic) material.

Example 6

Comparison of Anticancer Activity of CTO (858.F) with CAI+Orotic Acid (1:1)

The effect of CTO M.W. of 580.8 and CAI M.W. of 424.6+ Orotic Acid M.W. of 156.1, was studied in s.c.-implanted HT29 human colon tumor xenografts in male, athymic NCr-nu/nu mice. 6 week old mice were implanted with HT29 fragments and 13 days later were sorted in 3 groups of ten. For the next 14 days (13-26 days), Group 1 control (C) received the vehicle; Group 2=343 mg/kg/dose; Group 3=240 mg/kg/day CAI+103 mg/kg/day orotic acid. At 41 days, the mean tumor volume ($mm^3$) was measured as shown below:

Group 1 (Control)=1436 $mm^3$
Group 2 (CTO 343 mg/kg/day)=864 $mm^3$ (p=0.0050, Gr2 vs Gr 1)
Group 3 (CAI 250 mg/kg/day+Orotic Acid 103 mg/kg/day)= 1268 $mm^3$ (p=0.2706, Gr 3 vs Gr 1). These results suggest that CTO is more effective in inhibiting tumor growth than an equivalent amount of CAI and Orotic acid that are not chemically reacted. However, CAI+Orotic acid formulation did show some tumor inhibition.

Example 7

Comparison of CTO Given Orally as Solid in Capsule or as Liquid in PEG-400

The bioavailability of CTO (base:acid, 0.7:1.3) was determined by administering a single dose 685 mg/kg by capsule (Group 1) or by oral gavage in PEG400 (Group 2). Two dogs (1F/1M) were used in each group. Blood samples were collected at 0, 1, 2, 4, 8, 12, 24, 48, 72, and 92 hours. CAI was measured by HPLC/MS.

Group 1 receiving capsule: Plasma concentrations after 1 hr were 155 and 174 ng/ml for male and female dogs. $C_{max}$ was 5800 ng/ml at 12 hrs for male and 7950 ng/ml at 24 hrs for female. Half life was 18 hr and 22.7 hr and AUC values were 326 and 277 ug/mL, for male and female respectively.

Group 2 receiving gavage in PEG400: Plasma concentrations after 1 hr were 511 and 570 ng/ml for male and female dogs. $C_{max}$ was 6634 ng/ml at 24 hrs for male and 5350 ng/ml at 24 hr for female. Bioavailability was 81.8% of that in Group 1 (100%).

These results show that CTO given as solid in capsule had a better absorption pattern and bioavailability than CTO in PEG400. Based on these and additional results, CTO will be administered as solid in capsules to patients.

Example 8

CTO Given Orally to Mice Crosses the Blood Brain Barrier

CTO was given orally (in PEG400) to six week old mice sorted in two Groups of 6. Two doses were administered—Group 1=513 mg/kg; Group 2=342 mg/kg. Eight hours after treatment with CTO, the mice were euthanized for measurement of CTO concentration (as CAI) in brain tissue.

Results obtained were: Group 1-CAI levels were 15167±2372 ng/g tissue; Group 2 levels of CAI were 10950±1704 ng/g tissue, both in the therapeutic range (6000 ng/mL). Since the CTO was administered orally, these results indicate that CTO crosses the blood brain barrier and reaches the target organ, brain.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A polymorph form 1 of 5-amino-1-(4-(4-chlorobenzoyl)-3,5-dichlorobenzyl)-1,2,3-triazole-4-carboxamide bonded with orotic acid having a powder x-ray diffraction pattern comprising peaks at 2θ of 4.9, 20.2, 24.3, 26.5 and 28.7.

2. The polymorph of claim 1 having a XRPD pattern further comprising a peak at 19.7.

3. The polymorph according to claim 2 having a XRPD pattern further comprising a peak at 23.3.

4. The polymorph according to claim 3 having a XRPD pattern further comprising a peak at 28.0.

5. The polymorph according to claim 4 having a XRPD pattern further comprising a peak at 27.0.

6. The polymorph of claim 1 having a base:acid ratio is in the range of 0.7:1.3.

7. A polymorph form 2 of 5-amino-1-(4-(4-chlorobenzoyl)-3,5-dichlorobenzyl)-1,2,3-triazole-4-carboxamide bonded with orotic acid having a powder x-ray diffraction pattern comprising peaks at 2θ of 19.5, 23.2, 25, 28.7 and 29.

8. The polymorph of claim 7 having a XRPD pattern further comprising a peak at 21.9.

9. The polymorph according to claim 8 having a XRPD pattern further comprising a peak at 20.1.

10. The polymorph according to claim 9 having a XRPD pattern further comprising a peak at 19.1.

11. The polymorph according to claim 10 having a XRPD pattern further comprising a peak at 28.4.

12. The polymorph of claim 7 having a base:acid ratio is in the range of 0.7:1.3.

* * * * *